(12) United States Patent
O'Hagan et al.

(10) Patent No.: US 7,597,908 B2
(45) Date of Patent: *Oct. 6, 2009

(54) USE OF MICROPARTICLES WITH ADSORBED ANTIGEN TO STIMULATE IMMUNE RESPONSES

(75) Inventors: Derek O'Hagan, Berkeley, CA (US); Gary Van Nest, El Sobrante, CA (US); Gary S. Ott, Oakland, CA (US); John Barackman, San Leandro, CA (US); Jina Kazzaz, San Rafael, CA (US)

(73) Assignee: Novartis Vaccines and Diagnostics, Inc., Emeryville, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/189,104

(22) Filed: Jul. 3, 2002

(65) Prior Publication Data

US 2003/0049298 A1 Mar. 13, 2003

Related U.S. Application Data

(63) Continuation of application No. 09/015,652, filed on Jan. 29, 1998, now abandoned.

(60) Provisional application No. 60/036,316, filed on Jan. 30, 1997, provisional application No. 60/069,749, filed on Dec. 16, 1997.

(51) Int. Cl.
*A61K 9/18* (2006.01)
(52) U.S. Cl. .................................................. 424/491
(58) Field of Classification Search ............. 424/184.1, 424/489, 497, 490, 491, 1.11, 1.29, 408; 435/5; 430/139
See application file for complete search history.

(56) References Cited

U.S. PATENT DOCUMENTS

| | | | |
|---|---|---|---|
| 4,413,057 A | 11/1983 | Carlo et al. | 424/244.1 |
| 4,534,996 A | 8/1985 | Rembaum et al. | 427/498 |
| 5,010,183 A | 4/1991 | Macfarlane | 435/262 |
| 5,151,225 A | 9/1992 | Morgan et al. | 530/387.1 |
| 5,630,922 A | 5/1997 | Eswarakrishnan et al. | 204/499 |
| 5,643,605 A | 7/1997 | Cleland et al. | 424/279.1 |
| 5,660,854 A | 8/1997 | Haynes et al. | 424/450 |
| 5,693,522 A | 12/1997 | Chada et al. | 435/325 |
| 5,714,354 A | 2/1998 | Arnold et al. | 435/101 |
| 5,783,567 A | 7/1998 | Hedley et al. | 514/44 |
| 5,827,531 A | 10/1998 | Morrison et al. | 424/450 |
| 5,830,430 A | 11/1998 | Unger et al. | 424/1.21 |
| 5,846,538 A | 12/1998 | Cheever et al. | 424/185.1 |
| 5,855,913 A | 1/1999 | Hanes et al. | 424/489 |
| 5,869,103 A | 2/1999 | Yeh et al. | 425/801 |
| 5,869,445 A | 2/1999 | Cheever et al. | 514/2 |
| 5,871,747 A | 2/1999 | Gengoux-Sedlik et al. | 424/208.1 |
| 5,902,565 A | 5/1999 | Cox et al. | 424/1.29 |
| 6,015,567 A | 1/2000 | Hudziak et al. | 424/277.1 |
| 6,051,230 A | 4/2000 | Thorpe et al. | 424/178.1 |
| 6,086,901 A | 7/2000 | O'Hagan et al. | 424/283.1 |
| 6,207,646 B1 | 3/2001 | Krieg et al. | 514/44 |
| 6,270,769 B1 | 8/2001 | Raychaudhuri et al. | 424/184.1 |
| 6,468,982 B1 | 10/2002 | Weiner et al. | 514/44 |
| 6,753,015 B2 | 6/2004 | Fang et al. | 424/489 |
| 6,884,435 B1 | 4/2005 | O'Hagan et al. | 424/489 |
| 6,977,074 B2 | 12/2005 | Kundig et al. | 424/184.1 |
| 2003/0049298 A1 | 3/2003 | O'Hagan et al. | 424/418 |
| 2004/0022814 A1 | 2/2004 | O'Hagan et al. | 424/277.1 |

FOREIGN PATENT DOCUMENTS

| | | |
|---|---|---|
| WO | WO 91/02062 | 2/1991 |
| WO | WO 94/15635 | 7/1994 |
| WO | WO 94/28879 | 12/1994 |
| WO | WO 95/24929 | 9/1995 |
| WO | WO 95/32000 | 11/1995 |
| WO | WO 96/30514 | 3/1996 |
| WO | WO 96/20698 | 7/1996 |
| WO | WO 97/02810 | * 1/1997 |
| WO | WO 97/24447 | 7/1997 |
| WO | WO 98/10750 | 3/1998 |
| WO | WO 98/33487 | 8/1998 |
| WO | WO 98/40100 | 9/1998 |
| WO | WO 01/08636 | 2/2001 |

OTHER PUBLICATIONS

Coombes et al. Single dose, polymeric, microparticle-based vaccines: the influence of formulation conditions on the magnitude and duration of the immune response to a protein antigen.*
Coombes et al., Vaccines, vol. 14, No. 15, pp. 1429-1438.*
Kang et al. Evidence for non-V3-specific neutralizing antibodies that interfere with gp120/CD4 binding in human immunodeficiency virus 1-infected humans. Proc. Natl. Acad. Sci. USA., Jul. 1991, vol. 88, pp. 6171-6175.*

(Continued)

*Primary Examiner*—Emily M. Le
(74) *Attorney, Agent, or Firm*—Helen Lee; David Bonham

(57) ABSTRACT

The use of poly(lactide) or poly(lactide-co-glycolide) microparticles with adsorbed antigen is disclosed. The microparticles are useful for enhancing CTL responses to a selected antigen.

26 Claims, No Drawings

OTHER PUBLICATIONS

O'Hagan et al., "Long-term antibody responses in mice following subcutaneous Immunization with ovalbumin entrapped in biodegradable microparticles," Vaccine 11:965-969, 1993.

Coombes et al., "Single Dose, Polymeric, Microparticle-Based Vaccines: The Influence of Formulation Conditions on the Magnitude and Duration of the Immune REsponse to a Protein Antigen," Vaccine 14 (15):1429-1438 (1996).

Almeida, Antonio J. et al., "Poly(lactic acid) microspheres as immunological adjuvants for orally delivered cholera toxin B subunit," *Biochemcial Society Transactions* (1992) 20, p. 316S.

Almeida, Antonio, J., et al., "Immune Response To Nasal Delivery of Antigenically Intact Tetanus Toxoid Associated with Poly(L-lactic acid) Microspheres in Rats, Rabbits and Guinea-pigs," *J. Pharm. Pharmacol.* 1993, 45: 198-203, pp. 198-203.

Jackson, Raymond J., "Oral Vaccine Models: Multiple Delivery Systems Employing Tetanus Toxoid," *Annals New York Academy of Sciences*, 1994, vol. 730, pp. 217-234.

H.O. Alpar et al., Immune Responses to Mucosally Administered Tetanus Toxoid in Biodegradable Micropsheres, *Proceed. Intern. Symp. Control. Rel. Bioact. Mater*, 21 (1994), pp. 867-868.

Bertling, et al., "Use of Liposomes, Viral Capsids, and Nano-particles as DNA Carriers", *Biotechnology and Applied Bio-chemistry*, vol. 13, pp. 390-405 (1991).

Haynes et al., *AIDS Research and Human Retroviruses*, vol. 10, Supplement 2, 1994, pp. S42-S45.

P. Moingeon, "Cancer Vaccines," *Vaccine*, vol. 19, 2001, pp. 1305-1326.

Steven A. Rosenberg, "Progress in Human Tumour Immunology and Immunotherapy," *Nature*, vol. 411, May 17, 2001, pp. 380-384.

Said Dermime et al., "Cancer Vaccines and Immunotherapy," *British Medical Bulletin*, vol. 62, 2002, pp. 149-162.

Ian D. Davis et al., "Rational Approaches to Human Cancer Immunotherapy," *Journal of Leukocyte Biology*, vol. 73, Jan. 2003, pp. 3-29.

Igor Espinoza-Delgado, "Cancer Vaccines," *The Oncologist*, vol. 7 (suppl3), 2002, pp. 20-33.

Phil Gold et al., "Specific Carcinoembryonic Antigens of the Human Digestive System," *Journal of Experimental Medicine*, vol. 122, 1965, pp. 467-481.

Xiao-Juan Zhao et al., "$G_{D2}$ Oligosaccharide: Target for Cytotoxic T Lymphocytes," *Journal of Experimental Medicine*, vol. 182, Jul. 1995, pp. 67-74.

Phillip O. Livingston et al., "Carbohydrate Vaccines That Induce Antibodies Against Cancer. I. Rationale," *Cancer Immunol. Immunother.*. vol. 45, 1997, pp. 1-9.

Pascal Chaux et al., " Identification of MAGE-3 Epitopes Presented by HLA-DR Molecules to $CD4^+$ T Lymphocytes," *Journal of Experimental Medicine*, vol. 189, No. 5 Mar. 1, 1999, pp. 767-777.

Lloyd J. Old et al., "New Paths in Human Cancer Serology," *Journal of Experimental Medicine*, vol. 187, No. 8, Apr. 20, 1998, pp. 1163-1167.

Gustav Gaudernack, "T Cell Responses Against Mutant Ras: A Basis for Novel Cancer Vaccines," *Immunotechnology*, vol. 2, 1996, pp. 3-9.

Steven A. Rosenberg, "Cancer Vaccines Based on the Identification of Genes Encoding Cancer Regression Antigens," *Immunology Today*, vol. 18, No. 4, Apr. 1997, pp. 175-182.

Joyce Taylor-Papadimitriou et al., "Biology, Biochemistry and Immunology of Carcinoma-Associated Mucins," *Immunology Today*, vol. 18, No. 3, Mar. 1997, pp. 105-107.

Steven A. Rosenberg, "A New Era for Cancer Immunotherapy Based on the Genes that Encode Cancer Antigens," *Immunity*, vol. 10, Mar. 1999, pp. 281-287.

Matthias Theobald et al., "Targeting p53 as a General Tumor Antigen," *Proceedings of the National Academy of Sciences USA*, vol. 92, Dec. 1995, pp. 11993-11997.

Ugur Sahin et al., "Serological Identification of Human Tumor Antigens," *Current Opinion in Immunology*, vol. 9, 1997, pp. 709-716.

Benoit Van den Eyode et al., "New Tumor Antigens Recognized by T Cells," *Current Opinion in Immunology*, vol. 7, 1995, pp. 674-681.

Phillip O. Livingston et al., "Carbohydrate Vaccines That Induce Antibodies Against Cancer, 2. Previous Experience and Future Plans," *Cancer Immunol. Immunother.*, vol. 45, 1997, pp. 10-19.

Rienk Offringa et al., "Design and Evaluation of Antigen-Specific Vaccination Strategies Against Cancer," *Current Opinion in Immunology*, vol. 12, 2000, pp. 576-582.

Yunping Luo et al., "A DNA Vaccine Encoding Carcinoembryonic Antigen (CEA) Adsorbed onto Cationic Microparticles and Boosted with GM-CSF Induces T Cell— Mediated Protective Immunity Against Colon Cancer in CEA-Transgenic Mice" Abstract of presentation at the 2002 AACR Annual Meeting on Monday, Apr. 8, 2002, 1 p.

Christine Chavany, et al., "Adsorption of Oligonucleotides onto polyisohexylcyanoacrylate Nanoparticles Protects Them Against Nucleases and Increases Their Cellular Uptake," *Pharmaceutical research*, vol. 11, No. 9, 1994, pp. 1370-1378.

Elias Fattal, et al., "Biodegradable Polyalkylcyanocrylate Nanoparticles for the Delivery of Olionucleotides," *Journal of Controlled Release*, 53 (1998), pp. 137-143.

Duncan et al., "Poly (Lactide-Co-Glycolide) Microencapsulation of Vaccines for Mucosal Immunization," Mucosal Vaccine (Academic Press) pp. 159-173 (1996).

Eldridge et al. "Biodegradable and Biocompatible Poly (DL-Lactide-Co-Glycolide) Microspheres as an Adjuvant for Staphylococcal Enterotoxin B Toxoid Which Enhances the Level of Toxin-Neutralizing Antibodies," Infect. and Immunity, 1991, 59(9):2978-2986.

Eldridge et al., "New Advances in Vaccine Delivery Systems." Seminars in Hemotology 30(4) Suppl 4:16-25 (1993).

Higgins et al. "MF59 Adjuvant Enhances the Immunogenicity of Influenza Vaccine in BOth Young and Old Mice," Vaccine 14(6):478-484 (1996).

Men et al., "Induction of a Cytotoxin T Lymphocyte Response by Immunization With A Malaria Specific CTL Peptide Entrapped in Biodegradable Polymer Microspheres," Vaccine 15:1405-1432 (1997).

Moore et al., "Immunization With A Soluble Recombinant HIV Protein Entrapped In Biodegradel Micrparticles Induces HIV-Specific CD8+, Cytotoxic T Lymphocytes and CD4+ Tb1 Cells," Vaccine 13 (18):1741-1749 (1995).

Nakaoka et al., "Enhanced Antibody Production Through Sustained Antigen Release From Biodegradable Granules," J. Controlled Release 37:215-224 (1995).

O'Hagan et al. "Biodegradable Microparticles for Oral Immunization," Vaccine 11:(3)149-154 (1993).

Sah et al., "Continuous Release of Proteins From Biodegradable Microcapsules and In Vivo Evaluation of Their Potential as a Vaccine Adjuvant," J. Controlled Release 35:137-144 (1995).

Vordermeier et al., "Synthetic Delivery System for Tuberculosis Vaccines: Immunological Evaluation of the M. Tuberculosis 38 kDa Protein Entrapped in Biodegradable PLG Microparticles," Vaccine 13(16):1576-1582 (1995).

Powell et al. Eds., Vaccine Design: The Subunit and Adjuvant Approach. Plenum Press, NY, 1995, p. 183.

Briones et al., "The Preparation, Characterization, and Evaluation of Cationic Microparticles for DNA Vaccine Delivery," Pharmaceutical Research, vol. 18, No. 5, 2001, pp. 709-712.

\* cited by examiner

USE OF MICROPARTICLES WITH ADSORBED ANTIGEN TO STIMULATE IMMUNE RESPONSES

CROSS-REFERENCE TO RELATED APPLICATIONS

This application is a continuation of U.S. patent application Ser. No. 09/015,652 filed Jan. 29, 1998, now abandoned entitled "USE OF MICROPARTICLES WITH ADSORBED ANTIGEN TO STIMULATE IMMUNE RESPONSES," which is related to provisional patent applications Ser. Nos. 60/036,316, filed Jan. 30, 1997 and 60/069,749 filed Dec. 16, 1997, from which priority is claimed under 35 USC §119 (e)(1) and which applications are incorporated herein by reference in their entireties.

TECHNICAL FIELD

The present invention relates generally to vaccine compositions. In particular, the invention relates to the use of microparticles with adsorbed antigen for stimulating immunological responses, as well as to methods for making the microparticles.

BACKGROUND

Many pharmaceutical compositions include adjuvants in order to increase activity, antigenic potency and to enhance stability of the formulation. In this regard, vaccine compositions often include immunological adjuvants to enhance cell-mediated and humoral immune responses. For example, depot adjuvants are frequently used which adsorb) and/or precipitate administered antigens and which serve to retain the antigen at the injection site. Typical depot adjuvants include aluminum compounds and water-in-oil emulsions. However, depot adjuvants, although increasing antigenicity, often provoke severe persistent local reactions, such as granulomas, abscesses and scarring, when injected subcutaneously or intramuscularly. Other adjuvants, such as lipopolysacharrides and muramyl dipeptides, can elicit pyrogenic responses upon injection and/or Reiter's symptoms (influenza-like symptoms, generalized joint discomfort and sometimes anterior uveitis, arthritis and urethritis).

Despite the presence of such adjuvants, conventional vaccines often fail to provide adequate protection against the targeted pathogen. In this regard, there is growing evidence that vaccination against intracellular pathogens, such as a number of viruses, should target both the cellular and humoral arms of the immune system.

More particularly, cytotoxic T-lymphocytes (CTLs) play an important role in cell-mediated immune defense against intracellular pathogens such as viruses and tumor-specific antigens produced by malignant cells. CTLs mediate cytotoxicity of virally infected cells by recognizing viral determinants in conjunction with class I MHC molecules displayed by the infected cells. Cytoplasmic expression of proteins is a prerequisite for class I MHC processing and presentation of antigenic peptides to CTLs. However, immunization with killed or attenuated viruses often fails to produce the CTLs necessary to curb intracellular infection. Furthermore, conventional vaccination techniques against viruses displaying marked genetic heterogeneity and/or rapid mutation rates that facilitate selection of immune escape variants, such as HIV or influenza, are problematic. Accordingly, alternative techniques for vaccination have been developed.

Particulate carriers with adsorbed or entrapped antigens have been used in an attempt to elicit adequate immune responses. Such carriers present multiple copies of a selected antigen to the immune system and promote trapping and retention of antigens in local lymph nodes. The particles can be phagocytosed by macrophages and can enhance antigen presentation through cytokine release. Examples of particulate carriers include those derived from polymethyl methacrylate polymers, as well as microparticles derived from poly(lactides) and poly(lactide-co-glycolides), known as PLG. Polymethyl methacrylate polymers are nondegradable while PLG particles biodegrade by random nonenzymatic hydrolysis of ester bonds to lactic and glycolic acids which are excreted along normal metabolic pathways.

Recent studies have shown that PLG microparticles with entrapped antigens are able to elicit cell-mediated immunity. For example, microencapsulated human immunodeficiency virus (HIV) gp120 has been shown to induce HIV-specific CD4+ and CD8+ T-cell responses in mice (Moore et al., *Vaccine* (1995) 13:1741-1749). Additionally, both antibody and T-cell responses have been induced in mice vaccinated with a PLG-entrapped *Mycobacterium tuberculosis* antigen (Vordermeier et al., *Vaccine* (1995) 13:1576-1582).

While offering significant advantages over other more toxic systems, antigen-entrapped PLG microparticles suffer from some drawbacks. For example, the production of microparticles is difficult and involves the use of harsh chemicals that can denature the antigen and destroy the immunogenicity thereof. Furthermore, antigen instability can occur due to the high shear forces used to prepare small microparticles and due to interfacial effects within the emulsions used.

The use of antigens adsorbed to microparticles avoids these drawbacks. However, reports on the immunogenicity of microparticles with adsorbed antigen have been mixed. In fact, experimenters have postulated that antigens must be entrapped in microparticles in order to achieve an adequate adjuvant effect. See, e.g., Eldridge et al., *Infect. Immun.* (1991) 59:2978-2986; Eldridge et al., *Seminars in Hematology* (1993) 30:16-25; Nakaoka et al., *J. Controlled Release* (1995) 37:215-224; Sah et al., *J. Controlled Release* (1995) 35:137-144; and Duncan et al., "Poly(lactide-co-glycolide Microencapsulation of Vaccines for Mucosal Immunization" in *Mucosal Vaccines* (Academic Press, Inc., 1996).

More particularly, microparticle-encapsulated and -adsorbed ovalbumin have been shown to prime cellular immune responses in vivo and induce mucosal IgA responses when administered orally. However, entrapped antigen elicited better responses than adsorbed antigen (O'Hagan et al., *Vaccine* (1993) 11:149-154). Coombes et al., *Vaccine* (1996) 14:1429-1438 also describes experiments using both ovalbumin-encapsulated and -adsorbed microparticles. Antibody responses to the adsorbed antigen were significantly lower than those elicited by administration of entrapped ovalbumin. Finally, antigen-specific CTL responses have been reported in mice using a short synthetic peptide from the circumsporozoite protein of *Plasmodium berghei* microencapsulated in biodegradable microspheres or adsorbed on empty microspheres (Men et al., *Vaccine* (1997) 15:1405-1312).

However, none of the above studies describe the use of antigen-adsorbed microparticles, using viral antigens, to stimulate cell-mediated immune responses. Accordingly, there is a continued need for effective and safe adjuvants for use in a variety of pharmaceutical compositions and vaccines.

SUMMARY OF THE INVENTION

The inventors herein have found, surprisingly, that adsorbing selected viral antigens to microparticles derived from a poly(α-hydroxy acid), provides for superior immune responses. Accordingly, then, the invention is primarily directed to methods and compositions which include such microparticles, as well as to processes for producing the same. The use of microparticles with adsorbed antigens provides a safe and effective approach for enhancing the immunogenicity of a wide variety of antigens.

Accordingly, in one embodiment, the invention is directed to a composition comprising a selected viral antigen adsorbed to a poly(α-hydroxy acid) microparticle and a pharmaceutically acceptable excipient.

In an additional embodiment, the invention is directed to a method of immunization which comprises administering to a vertebrate subject a therapeutically effective amount of the microparticle composition above.

In yet an additional embodiment, the invention is directed to a method for eliciting a cellular immune response in a vertebrate subject comprising administering to a vertebrate subject a therapeutically effective amount of a selected viral antigen adsorbed to a poly(α-hydroxy acid) microparticle.

In yet a further embodiment, the invention is directed to a method of producing a composition comprising:
(a) providing a viral antigen;
(b) adsorbing the viral antigen to a poly(α-hydroxy acid) microparticle; and
(c) combining the microparticle with the adsorbed antigen with a pharmaceutically acceptable excipient.

In particularly preferred embodiments, the microparticles above are formed from poly(D,L-lactide-co-glycolide).

These and other embodiments of the present invention will readily occur to those of ordinary skill in the art in view of the disclosure herein.

DETAILED DESCRIPTION OF THE INVENTION

The practice of the present invention will employ, unless otherwise indicated, conventional methods of chemistry, biochemistry, molecular biology, immunology and pharmacology, within the skill of the art. Such techniques are explained fully in the literature. See, e.g., *Remington's Pharmaceutical Sciences*, 18th Edition (Easton, Pa.: Mack Publishing Company, 1990); *Methods In Enzymology* (S. Colowick and N. Kaplan, eds., Academic Press, Inc.); and *Handbook of Experimental Immunology*, Vols. I-IV (D. M. Weir and C. C. Blackwell, eds., 1986, Blackwell Scientific Publications); and Sambrook, et al., *Molecular Cloning: A Laboratory Manual* (2nd Edition, 1989).

All publications, patents and patent applications cited herein, whether supra or infra, are hereby incorporated by reference in their entirety.

As used in this specification and the appended claims, the singular forms "a," "an" and "the" include plural references unless the content clearly dictates otherwise.

A. Definitions

In describing the present invention, the following terms will be employed, and are intended to be defined as indicated below.

The term "microparticle" as used herein, refers to a particle of about 100 nm to about 150 μm in diameter, more preferably about 200 nm to about 30 μm in diameter, and most preferably about 500 nm to about 10 μm in diameter. Preferably, the microparticle will be of a diameter that permits parenteral administration without occluding needles and capillaries. Microparticle size is readily determined by techniques well known in the art, such as photon correlation spectroscopy, laser diffractometry and/or scanning electron microscopy. Microparticles for use herein will be formed from materials that are sterilizable, non-toxic and biodegradable. Such materials include, without limitation, poly(α-hydroxy acid), polyhydroxybutyric acid, polycaprolactone, polyorthoester, polyanhydride. Preferably, microparticles for use with the present invention are derived from a poly(α-hydroxy acid), in particular, from a poly(lactide) ("PLA") or a copolymer of D,L-lactide and glycolide or glycolic acid, such as a poly(D,L-lactide-co-glycolide) ("PLG" or "PLGA"), or a copolymer of D,L-lactide and caprolactone. The microparticles may be derived from any of various polymeric starting materials which have a variety of molecular weights and, in the case of the copolymers such as PLG, a variety of lactide:glycolide ratios, the selection of which will be largely a matter of choice, depending in part on the coadministered antigen. These parameters are discussed more fully below.

By "antigen" is meant a molecule which contains one or more epitopes that will stimulate a host's immune system to make a cellular antigen-specific immune response when the antigen is presented, or a humoral antibody response. Normally, an epitope will include between about 3-15, generally about 5-15, amino acids. For purposes of the present invention, antigens can be derived from any of several known viruses. Furthermore, for purposes of the present invention, an "antigen" refers to a protein which includes modifications, such as deletions, additions and substitutions (generally conservative in nature), to the native sequence, so long as the protein maintains the ability to elicit an immunological response. These modifications may be deliberate, as through site-directed mutagenesis, or may be accidental, such as through mutations of hosts which produce the antigens.

An "immunological response" to an antigen or composition is the development in a subject of a humoral and/or a cellular immune response to molecules present in the composition of interest. For purposes of the present invention, a "humoral immune response" refers to an immune response mediated by antibody molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the intracellular destruction of intracellular microbes, or the lysis of cells infected with such microbes. Another aspect of cellular immunity involves an antigen-specific response by helper T-cells. Helper T-cells act to help stimulate the function, and focus the activity of, nonspecific effector cells against cells displaying peptide antigens in association with MHC molecules on their surface. A "cellular immune response" also refers to the production of cytokines, chemokines and other such molecules produced by activated T-cells and/or other white blood cells, including those derived from CD4+ and CD8+ T-cells.

A composition or vaccine that elicits a cellular immune response may serve to sensitize a vertebrate subject by the presentation of antigen in association with MHC molecules at the cell surface. The cell-mediated immune response is directed at, or near, cells presenting antigen at their surface. In addition, antigen-specific T-lymphocytes can be generated to allow for the future protection of an immunized host.

The ability of a particular antigen or composition to stimulate a cell-mediated immunological response may be determined by a number of assays, such as by lymphoproliferation (lymphocyte activation) assays, CTL cytotoxic cell assays, or by assaying for T-lymphocytes specific for the antigen in a sensitized subject. Such assays are well known in the art. See, e.g., Erickson et al., *J. Immunol.* (1993) 151:4189-4199; Doe et al., *Eur. J. Immunol.* (1994) 24:2369-2376; and the examples below.

Thus, an immunological response as used herein may be one which stimulates the production of CTLs, and/or the production or activation of helper T-cells. The antigen of interest may also elicit an antibody-mediated immune response. Hence, an immunological response may include one or more of the following effects: the production of antibodies by B-cells; and/or the activation of suppressor T-cells and/or γδ T-cells directed specifically to an antigen or antigens present in the composition or vaccine of interest. These responses may serve to neutralize infectivity, and/or mediate antibody-complement, or antibody dependent cell cytotoxicity (ADCC) to provide protection to an immunized host. Such responses can be determined using standard immunoassays and neutralization assays, well known in the art.

A vaccine composition which contains a selected antigen adsorbed to a microparticle, displays "enhanced immunogenicity" when it possesses a greater capacity to elicit an immune response than the immune response elicited by an equivalent amount of the antigen when delivered without association with the microparticle. Thus, a vaccine composition may display "enhanced immunogenicity" because the antigen is more strongly immunogenic by virtue of adsorption to the microparticle, or because a lower dose of antigen is necessary to achieve an immune response in the subject to which it is administered. Such enhanced immunogenicity can be determined by administering the microparticle/antigen composition, and antigen controls to animals and comparing antibody titers against the two using standard assays such as radioimmunoassay and ELISAs, well known in the art.

The terms "effective amount" or "pharmaceutically effective amount" of an antigen/microparticle, as provided herein, refer to a nontoxic but sufficient amount of the antigen/microparticle to provide the desired immunological response and corresponding therapeutic effect. As will be pointed out below, the exact amount required will vary from subject to subject, depending on the species, age, and general condition of the subject, the severity of the condition being treated, and the particular antigen of interest, mode of administration, and the like. An appropriate "effective" amount in any individual case may be determined by one of ordinary skill in the art using routine experimentation.

By "vertebrate subject" is meant any member of the subphylum cordata, including, without limitation, mammals such as cattle, sheep, pigs, goats, horses, and man; domestic animals such as dogs and cats; and birds, including domestic, wild and game birds such as cocks and hens including chickens, turkeys and other gallinaceous birds. The term does not denote a particular age. Thus, both adult and newborn animals are intended to be covered. By "pharmaceutically acceptable" or "pharmacologically acceptable" is meant a material which is not biologically or otherwise undesirable, i.e., the material may be administered to an individual along with the microparticle formulation without causing any undesirable biological effects or interacting in a deleterious manner with any of the components of the composition in which it is contained.

By "physiological pH" or a "pH in the physiological range" is meant a pH in the range of approximately 7.2 to 8.0 inclusive, more typically in the range of approximately 7.2 to 7.6 inclusive.

As used herein, "treatment" refers to any of (i) the prevention of infection or reinfection, as in a traditional vaccine, (ii) the reduction or elimination of symptoms, and (iii) the substantial or complete elimination of the pathogen in question. Treatment may be effected prophylactically (prior to infection) or therapeutically (following infection).

B. General Methods

Central to the present invention is the discovery that PLA and PLG microparticles with adsorbed viral antigens can generate cell-mediated immune responses in a vertebrate subject. The ability of the antigen/microparticles of the present invention to elicit a cell-mediated immune response against a selected antigen provides a powerful tool against infection by a wide variety of viruses. The antigen/microparticles of the present invention can be incorporated into vaccine compositions. Furthermore, the adjuvant formulations of the invention may be used to enhance the activity of antigens produced in vivo, i.e., in conjunction with DNA immunization.

Although the individual components of the vaccine compositions and methods described herein were known, it was unexpected and surprising that such combinations would produce potent cell-mediated immune responses beyond levels achieved when the components were used separately. Thus, in addition to a conventional antibody response, the system herein described can provide for, e.g., the association of the expressed antigens with class I MHC molecules such that an in vivo cellular immune response to the antigen of interest can be mounted which stimulates the production of CTLs to allow for future recognition of the antigen. Furthermore, the methods may elicit an antigen-specific response by helper T-cells. Accordingly, the methods of the present invention will find use with any antigen for which cellular and/or humoral immune responses are desired, including antigens derived from viral pathogens that may induce antibodies, T-cell helper epitopes and T-cell cytotoxic epitopes. Such antigens include, but are not limited to, those encoded by human and animal viruses and can correspond to either structural or non-structural proteins.

The technique is particularly useful for immunization against intracellular viruses which normally elicit poor immune responses. For example, the present invention will find use for stimulating an immune response against a wide variety of proteins from the herpesvirus family, including proteins derived from herpes simplex virus (HSV) types 1 and 2, such as HSV-1 and HSV-2 glycoproteins gB, gD and gH; antigens derived from varicella zoster virus (VZV), Epstein-Barr virus (EBV) and cytomegalovirus (CMV) including CMV gB and gH; and antigens derived from other human herpesviruses such as HHV6 and HHV7. (See, e.g. Chee et al., *Cytomegaloviruses* (J. K. McDougall, ed., Springer-Verlag 1990) pp. 125-169, for-a review of the protein coding content of cytomegalovirus; McGeoch et al., *J. Gen. Virol.* (1988) 69:1531-1574, for a discussion of the various HSV-1 encoded proteins; U.S. Pat. No. 5,171,568 for a discussion of HSV-1 and HSV-2 gB and gD proteins and the genes encoding therefor; Baer et al., *Nature* (1984) 310:207-211, for the identification of protein coding sequences in an EBV genome; and Davison and Scott, *J. Gen. Virol.* (1986) 67:1759-1816, for a review of VZV.)

Antigens from the hepatitis family of viruses, including hepatitis A virus (HAV), hepatitis B virus (HBV), hepatitis C virus (HCV), the delta hepatitis virus (HDV), hepatitis E virus (HEV) and hepatitis G virus (HGV), can also be conveniently used in the techniques described herein. By way of example, the viral genomic sequence of HCV is known, as are methods for obtaining the sequence. See, e.g., International Publication Nos. WO 89/04669; WO 90/11089; and WO 90/14436. The HCV genome encodes several viral proteins, including E1 (also known as E) and E2 (also known as E2/NSI) and an N-terminal nucleocapsid protein (termed "core") (see, Houghton et al., *Hepatology* (1991) 14:381-388, for a discussion of HCV proteins, including E1 and E2). Each of these proteins, as well as antigenic fragments thereof, will find use in the present methods. Similarly, the sequence for the δ-antigen from HDV is known (see, e.g., U.S. Pat. No. 5,378,814) and this antigen can also be conveniently used in the present methods. Additionally, antigens derived from HBV, such as the core antigen, the surface antigen, sAg, as well as the presurface sequences, pre-S1 and pre-S2 (formerly called pre-S), as well as combinations of the above, such as sAg/pre-S1, sAg/pre-S2, sAg/pre-S1/pre-S2, and pre-S1/pre-S2, will find use herein. See, e.g., "HBV Vaccines—from the laboratory to license: a case study" in Mackett, M. and Williamson, J. D., *Human Vaccines and Vaccination*, pp. 159-176, for a discussion of HBV structure; and U.S. Pat. Nos. 4,722,840, 5,098,704, 5,324,513, incorporated herein by reference in their entireties; Beames et al., *J. Virol.* (1995) 69:6833-6838, Birnbaum et al., *J. Virol.* (1990) 64:3319-3330; and Zhou et al., *J. Virol.* (1991) 65:5457-5464.

Antigens derived from other viruses will also find use in the claimed methods, such as without limitation, proteins from members of the families Picornaviridae (e.g., polioviruses, etc.); Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae (e.g., HTLV-I; HTLV-II; HIV-1 (also known as HTLV-III, LAV, ARV, hTLR, etc.)), including but not limited to antigens from the isolates $HIV_{IIIb}$, $HIV_{SF2}$, $HIV_{LAV}$, $HIV_{LAI}$, $HIV_{MN}$); $HIV-1_{CM235}$, $HIV-1_{US4}$; HIV-2; simian immunodeficiency virus (SIV) among others. Additionally, antigens may also be derived from human papillomavirus (HPV) and the tick-borne encephalitis viruses. See, e.g. Virology, 3rd Edition (W. K. Joklik ed. 1988); *Fundamental Virology*, 2nd Edition (B. N. Fields and D. M. Knipe, eds. 1991), for a description of these and other viruses.

More particularly, the gp120 envelope proteins from any of the above HIV isolates, including members of the various genetic subtypes of HIV, are known and reported (see, e.g., Myers et al., Los Alamos Database, Los Alamos National Laboratory, Los Alamos, N.Mex. (1992); Myers et al., *Human Retroviruses and Aids*, 1990, Los Alamos, N.Mex.: Los Alamos National Laboratory; and Modrow et al., *J. Virol.* (1987) 61:570-578, for a comparison of the envelope sequences of a variety of HIV isolates) and antigens derived from any of these isolates will find use in the present methods. Furthermore, the invention is equally applicable to other immunogenic proteins derived from any of the various HIV isolates, including any of the various envelope proteins such as gp160 and gp41, gag antigens such as p24gag and p55gag, as well as proteins derived from the pol region.

As explained above, influenza virus is another example of a virus for which the present invention will be particularly useful. Specifically, the envelope glycoproteins HA and NA of influenza A are of particular interest for generating an immune response. Numerous HA subtypes of influenza A have been identified (Kawaoka et al., *Virology* (1990) 179: 759-767; Webster et al., "Antigenic variation among type A influenza viruses," p. 127-168. In: P. Palese and D. W. Kingsbury (ed.), *Genetics of influenza viruses*. Springer-Verlag, New York). Thus, proteins derived from any of these isolates can also be used in the immunization techniques described herein.

It is readily apparent that the subject invention can be used to mount an immune response to a wide variety of antigens and hence to treat or prevent a large number of diseases.

The selected antigen is adsorbed to a microparticle for subsequent delivery. Biodegradable polymers for manufacturing microparticles for use with the present invention are readily commercially available from, e.g., Boehringer Ingelheim, Germany and Birmingham Polymers, Inc., Birmingham, Ala. For example, useful polymers for forming the microparticles herein include those derived from polyhydroxybutyric acid; polycaprolactone; polyorthoester; polyanhydride; as well as a poly(α-hydroxy acid), such as poly(L-lactide), poly(D,L-lactide) (both known as "PLA" herein), poly(hydoxybutyrate), copolymers of D,L-lactide and glycolide, such as poly(D,L-lactide-co-glycolide) (designated as "PLG" or "PLGA" herein) or a copolymer of D,L-lactide and caprolactone. Particularly preferred polymers for use herein are PLA and PLG polymers. These polymers are available in a variety of molecular weights, and the appropriate molecular weight for a given antigen is readily determined by one of skill in the art. Thus, e.g., for PLA, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000.

If a copolymer such as PLG is used to form the microparticles, a variety of lactide:glycolide ratios will find use herein and the ratio is largely a matter of choice, depending in part on the coadministered antigen and the rate of degradation desired. For example, a 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component. It is readily apparent that a suitable ratio of lactide:glycolide is easily determined by one of skill in the art based on the nature of the antigen and disorder in question. Moreover, mixtures of microparticles with varying lactide:glycolide ratios will find use in the formulations in order to achieve the desired release kinetics for a given antigen and to provide for both a primary and secondary immune response. Degradation rate of the microparticles of the present invention can also be controlled by such factors as polymer molecular weight and polymer crystallinity. PLG copolymers with varying lactide:glycolide ratios and molecular weights are readily available commercially from a number of sources including from Boehringer Ingelheim, Germany and Birmingham Polymers, Inc., Birmingham, Ala. These polymers can also be synthesized by simple polycondensation of the lactic acid component using techniques well known in the art, such as described in Tabata et al., *J. Biomed. Mater. Res.* (1988) 22:837-858.

The antigen-containing microparticles are prepared using any of several methods well known in the art. For example, double emulsion/solvent evaporation techniques, such as described in U.S. Pat. No. 3,523,907 and Ogawa et al., *Chem. Pharm. Bull.* (1988) 36:1095-1103, can be used herein to make the microparticles. These techniques involve the formation of a primary emulsion consisting of droplets of polymer solution, which is subsequently mixed with a continuous aqueous phase containing a particle stabilizer/surfactant.

More particularly, a water-in-oil-in-water (w/o/w) solvent evaporation system can be used to form the microparticles, as described by O'Hagan et al., *Vaccine* (1993) 11:965-969 and Jeffery et al., Pharm. Res. (1993) 10:362. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2-15%, more preferably about a 4-10% and most preferably, a 6% solution, in organic solvent. The polymer solution is emulsified using e.g, an homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2-15% solution, more typically about a 4-10% solution. The mixture is then homogenized to produce a-stable w/o/w double emulsion. Organic solvents are then evaporated.

The formulation parameters can be manipulated to allow the preparation of small (<5 µm) and large (>30 µm) microparticles. See, e.g., Jeffery et al., *Pharm. Res.* (1993) 10:362-368; McGee et al., *J. Microencap.* (1996). For example, reduced agitation results in larger microparticles, as does an increase in internal phase volume. Small particles are produced by low aqueous phase volumes with high concentrations of PVA.

Microparticles can also be formed using spray-drying and coacervation as described in, e.g., Thomasin et al., *J. Controlled Release* (1996) 41:131; U.S. Pat. No. 2,800,457; Masters, K. (1976) *Spray Drying* 2nd Ed. Wiley, New York; air-suspension coating techniques, such as pan coating and Wurster coating, as described by Hall et al., (1980) The "Wurster Process" in *Controlled Release Technologies: Methods, Theory, and Applications* (A. F. Kydonieus, ed.), Vol. 2, pp. 133-154 CRC Press, Boca Raton, Fla. and Deasy, P. B., *Crit. Rev. Ther. Drug Carrier Syst.* (1988) S(2):99-139; and ionic gelation as described by, e.g., Lim et al., *Science* (1980) 210:908-910.

Particle size can be determined by, e.g., laser light scattering, using for example, a spectrometer incorporating a helium-neon laser. Generally, particle size is determined at room temperature and involves multiple analyses of the sample in question (e.g., 5-10 times) to yield an average value for the particle diameter. Particle size is also readily determined using scanning electron microscopy (SEM).

Following preparation, microparticles can be stored as is or freeze-dried for further use. In order to adsorb antigen to the microparticles, the microparticle preparation is simply mixed with the antigen of interest and the resulting formulation can again be lyophilized prior to use. Protein content of the microparticles can be determined using standard techniques.

A particularly preferred method for adsorbing antigen onto prepared microparticles is as follows. Microparticles are rehydrated and dispersed to an essentially monomeric suspension of microparticles using dialyzable detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methylglucamide (MEGA-10); cholic acid; sodium cholate; deoxycholic acid; sodium deoxycholate; taurocholic acid; sodium taurocholate; taurodeoxycholic acid; sodium taurodeoxycholate; 3-[(3-cholamidopropyl)dimethylammonio]-1-propane-sulfonate (CHAPS); 3-[(3-cholamidopropyl)dimethylammonio]-2-hydroxy-1-propane-sulfonate (CHAPSO); N-dodecyl-N,N-dimethyl-3-ammonio-1-propane-sulfonate (ZWITTERGENT 3-12); N,N-bis-(3-D-gluconeamidopropyl)-deoxycholamide (DEOXY-BIGCHAP); N-octylglucoside; sucrose monolaurate; glycocholic acid/sodium glycocholate; laurosarcosine (sodium salt); glycodeoxycholic acid/sodium glycodeoxycholate. The above detergents are commercially available from e.g., Sigma chemical Co., St. Louis, Mo. Generally, a ratio of about 0.0156:1 detergent to microparticle (w:w) will be used, more preferably about 0.625:1, even more preferably about 0.25:1 and most preferably about 1:1 to 2:1, detergent to microparticle (w:w).

The microparticle/detergent mixture is then physically ground, e.g., using a ceramic mortar and pestle, until a smooth slurry is formed. An appropriate aqueous buffer, such as phosphate buffered saline (PBS) or Tris buffered saline, is then added and the resulting mixture sonicated or homogenized until the microparticles are fully suspended. The antigen of interest is then added to the microparticle suspension and the system dialyzed to remove detergent. The polymer microparticles and detergent system are preferably chosen such that the antigen of interest will adsorb to the microparticle surface while still maintaining activity of the antigen. The resulting microparticles containing surface adsorbed antigens may be washed free of unbound antigen and stored as a suspension in an appropriate buffer formulation, or lyophilized with the appropriate excipients, as described further below.

Once the antigen/microparticles are produced, they are formulated into vaccine compositions to treat and/or prevent a wide variety of viral disorders, as described above. The compositions will generally include one or more "pharmaceutically acceptable excipients or vehicles" such as water, saline, glycerol, polyethyleneglycol, hyaluronic acid, ethanol, etc. Additionally, auxiliary substances, such as wetting or emulsifying agents, biological buffering substances, and the like, may be present in such vehicles. A biological buffer can be virtually any solution which is pharmacologically acceptable and which provides the formulation with the desired pH, i.e., a pH in the physiological range. Examples of buffer solutions include saline, phosphate buffered saline, Tris buffered saline, Hank's buffered saline, and the like.

Adjuvants may be used to enhance the effectiveness of the pharmaceutical compositions. The adjuvants may be administered concurrently with the microparticles of the present invention, e.g., in the same composition or in separate compositions. Alternatively, an adjuvant may be administered prior or subsequent to the microparticle compositions of the present invention. Such adjuvants include, but are not limited to: (1) aluminum salts (alum), such as aluminum hydroxide, aluminum phosphate, aluminum sulfate, etc.; (2) oil-in-water emulsion formulations (with or without other specific immunostimulating agents such as muramyl peptides (see below) or bacterial cell wall components), such as for example (a) MF59 (International Publication No. WO 90/14837), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi™ adjuvant system (RAS), (Ribi Immunochem, Hamilton, Mont.) containing 2% Squalene, 0.2% Tween 80, and one or more bacterial cell wall components from the group consisting of monophosphorylipid A (MPL), trehalose dimycolate (TDM), and cell wall skeleton (CWS), preferably MPL+CWS (Detox™) (for a further discussion of suitable submicron oil-in-water emulsions for use herein, see commonly owned, patent application attorney docket no. 2300-1397, filed on even date herewith); (3) saponin adjuvants, such as Stimulon™ (Cambridge Bioscience, Worcester, Mass.) may be used or particle generated therefrom such as ISCOMs (immunostimulating complexes); (4) Complete Freunds Adjuvant (CFA) and Incomplete Freunds Adjuvant (IFA); (5) cytokines, such as interleukins (IL-1, IL-2, etc.), macrophage colony stimulating factor (M-CSF), tumor necrosis factor (TNF), etc.; and (6) other substances that act as immunostimulating agents to enhance the effectiveness of the composition. Alum and MF59 are preferred.

Muramyl peptides include, but are not limited to, N-acetyl-muramyl-L-threonyl-D-isoglutamine (thr-MDP), N-acteyl-normuramyl-L-alanyl-D-isogluatme (nor-MDP), N-acetyl-muramyl-L-alanyl-D-isogluatminyl-L-alanine-2-(l'-2'-dipalmitoyl-sn-glycero-3-huydroxyphosphoryloxy)-ethylamine (MTP-PE), etc.

The compositions will comprise a "therapeutically effective amount" of the antigen of interest. That is, an amount of antigen/microparticle will be included in the compositions which will cause the subject to produce a sufficient immunological response in order to prevent, reduce or eliminate symptoms. The exact amount necessary will vary, depending on the subject being treated; the age and general condition of the subject to be treated; the capacity of the subject's immune system to synthesize antibodies; the degree of protection desired; the severity of the condition being treated; the particular antigen selected and its mode of administration, among other factors. An appropriate effective amount can be readily determined by one of skill in the art. Thus, a "therapeutically effective amount" will fall in a relatively broad range that can be determined through routine trials. For example, for purposes of the present invention, an effective dose will typically range from about 1 μg to about 100 mg, more preferably from about 10 μg to about 1 mg, and most preferably about 50 μg to about 500 μg of the antigen delivered per dose.

Once formulated, the compositions of the invention can be administered parenterally, e.g., by injection. The compositions can be injected either subcutaneously, intraperitoneally, intravenously or intramuscularly. Other modes of administration include oral and pulmonary administration, suppositories, and transdermal applications. Dosage treatment may be a single dose schedule or a multiple dose schedule. A multiple dose schedule is one in which a primary course of vaccination may be with 1-10 separate doses, followed by other doses given at subsequent time intervals, chosen to maintain and/or reinforce the immune response, for example at 1-4 months for a second dose, and if needed, a subsequent dose(s) after several months. The dosage regimen will also, at least in part, be determined by the need of the subject and be dependent on the judgment of the practitioner. Furthermore, if prevention of disease is desired, the vaccines are generally administered prior to primary infection with the pathogen of interest. If treatment is desired, e.g., the reduction of symptoms or recurrences, the vaccines are generally administered subsequent to primary infection.

C. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

EXAMPLE 1

Preparation of HA-Entrapped Microspheres Using a Solvent Evaporation Technique

In a 15 ml glass test tube was placed 0.5 ml 5 mg/ml Influenza A/Beijing93 hemagglutinin antigen (HA) and 5 ml 6% w:w PLG (poly D,L-lactide-co-glycolide) in dichloromethane, 50:50 mol ratio lactide to glycolide, MW average=70-100 kDa, (Medisorb Technologies International). The solution was homogenized for 2 minutes at high rpm using a hand held homogenizer. The homogenate was added to 20 ml 8% polyvinyl alcohol (PVA) (12-23 kDa) in a 100 ml glass beaker. This was homogenized for two minutes at a 10,000 rpm using a bench scale homogenizer equipped with a 20 mm diameter generator. The solution was stirred at room temperature at a moderate rate using a magnetic stir bar until the solvents were evaporated. Microspheres were resuspended in water and washed several times with water, using centrifugation to pellet microspheres between washes. Microspheres were dried in the presence of desiccant (Dririte $CaSO_4$) under vacuum. Mean volume size was determined to be 0.9 μm by laser diffraction measurement. Protein content of the microspheres was determined to be 0.5% w:w by amino acid compositional analysis.

EXAMPLE 2

Preparation of HA-Adsorbed Microspheres Using a Solvent Evaporation Technique

In a 100 ml glass beaker was placed 10 ml water and 100 ml 4% w:w PLG in dichloromethane, 50:50 mol ratio lactide to glycolide, MW average=80 kDa (Boehringer Ingelheim). The solution was homogenized for three minutes at 10,000 rpm using a bench scale homogenizer equipped with a 35 mm diameter generator. 400 ml 10% PVA (12-23 kDa) was added while continuing to homogenize for an additional three minutes. The solution was stirred at room temperature overnight, at a moderate rate using a magnetic stir bar, until the dichloromethane evaporated. Microspheres were washed several times with water using centrifugation to pellet microspheres between washes and the microspheres freeze-dried. 123 mg of freeze-dried microspheres were added to 2.4 ml 1 mg/ml Influenza A/Beiging93 HA antigen in a glass vial and freeze-dried after overnight incubation at 4° C. Mean volume size was determined to be 0.34 um by laser diffraction measurement. Protein content was approximately 2% w:w after freeze-drying.

EXAMPLE 3

Immunogenicity of HA-Entrapped and -Adsorbed Microspheres

The HA-entrapped and adsorbed microspheres, produced as described above, were administered to mice and the mice were boosted after 28 days, as shown in Table 1. A total dose of 4 μg of HA-adsorbed microparticles was administered. A total dose of HA-entrapped microparticles was administered. Serum was collected at day 42 and evaluated for total HIA and total Ig. The results are shown in Table 1. As can be seen, the HA-adsorbed microparticles were more immunogenic than the HA-entrapped formulation.

TABLE 1

| Animal Group | μg HA prime/boost day 0/day 28 | Serum Anti-HA Response at Day 42 | |
|---|---|---|---|
| | | Total Ig | HIA |
| HA-adsorbed | 2/2 | 7.00E + 05 | 1280 |
| HA-encapsulated | 1/4 | 1.50E + 05 | 160 |

EXAMPLE 4

Preparation of HA-Adsorbed Microspheres Using a Spray Drying Technique

2% (w:w) poly (d,l-lactide-co-glycolide) (Medisorb Technologies, 50:50 mol ratio lactide to glycolide, 70-100 Kdal MW or equivalent) in dichloromethane was spray dried using a Buchi mini spray-dryer (model B-191) at an inlet temperature of 67-68° C., an outlet temperature of 55° C., a spray pressure of 80 PSI, and a spray flow of 800 L/hr. Resulting microparticles were determined to be 1-5 μm in diameter by light microscopy examination against size standards.

450 mg of the spray dried microparticles and nine ml 10% MEGA-10 detergent (2:1 w:w ratio MEGA-10 to microparticles) were placed in a ceramic mortar. The mixture was ground using a ceramic pestle until a smooth slurry formed. 22.5 ml of phosphate buffered saline (PBS) were added and the mixture was homogenized three minutes using a bench scale homogenizer at 25,000 RPM with a 10 mm diameter generator, until microparticles were fully resuspended.

A/Beijing HA bulk antigen, containing 1 mg/ml protein content as assayed by a bicinchoninic acid (BCA) protein assay (Pierce, Rockford, Ill.), and approximately 0.2 mg/ml HA activity, as assayed by single radial immunodiffusion (SRID) was adsorbed to the microparticles as follows. 6 ml A/Beijing HA bulk antigen was diluted with 9.6 ml PBS and then added to 8.4 ml of the microparticle slurry (final composition: 0.25 mg/ml protein, 120 mg microparticles, 1% w:v MEGA-10, 5% w:w protein:particle ratio). The mixture was dialyzed extensively using a 50,000 molecular weight cutoff cellulose dialysis membrane against PBS until MEGA-10 was removed, as measured by colorimetric assay. The dialysate was removed from the dialysis bag and centrifuged to pellet microparticles. Supernatant was removed and discarded and the microparticles washed with two changes of PBS, with centrifuging between washes. 30 ml PBS were used per wash. Protein load was measured by standard methods, using BCA at approximately 1.4% protein content by weight microparticles.

EXAMPLE 5

Immunogenicity of HA-Adsorbed Microspheres Produced by Spray Drying

In order to test the immunogenicity of the microparticles produced in Example 4, groups of Balb/C mice (n=10) were immunized intramuscularly according to the schedule shown in Table 2. Priming and boosting were performed one month apart. Dosing was done with A/Beijing antigen based on HA activity (SRID) either as a soluble antigen in PBS alone, or surface adsorbed to microparticles. Serum samples were taken two weeks and four weeks post boost immunization and assayed for A/Beijing specific total Ig titers by a calorimetric based ELISA. Serum samples were further evaluated for hemagglutination inhibition activity (HI). Results of the ELISA and HI assays are summarized in Table 2. As indicated, intramuscular immunization with HA-adsorbed microparticles resulted in equivalent or measurably higher Ig and HI titers than immunization with HA alone.

A/Beijing HA encapsulated into PLG microparticles using a standard microencapsulation technique were shown to elicit poor HI responses after intramuscular administration indicating that denaturation of HA occurred during the encapsulation process. Therefore, presentation of antigen on the surface of microparticles presents advantages over microencapsulation of the antigen and surprisingly, shows an adjuvant effect.

TABLE 2

| | Immunization Schedule | | Serum Titers | | | |
|---|---|---|---|---|---|---|
| | | | Two Weeks Post Boost | | Four Weeks Post Boost | |
| Group # | Prime (Day 0) | Boost (Day 28) | Total Ig | HI | Total Ig | HI |
| 1 | | 14 μg HA | 52,000 | 150 | 207,000 | 160 |
| 2 | | 14 μg HA (HA μ-particles) | 236,000 | 320 | 415,000 | 320 |
| 3 | 1 μg HA | 14 μg HA | 1,160,000 | 1,280 | 911,000 | 1,280 |
| 4 | 1 μg HA | 14 μg HA (HA μ-particles) | 1,310,000 | 2,560 | 1,360,000 | 1,280 |

EXAMPLE 6

Preparation of PLG-Entrapped HSVgD2 Microspheres

HSVgD2-entrapped PLG microparticles were prepared by a solvent evaporation technique, generally as described above. Briefly, the microparticles with a 1% w/w antigen loading level were prepared by adding 2 ml of antigen solution and emulsifying at high speed using a silverson homogenizer, with 10 ml of a 5% w/v PLG polymer solution in methylene chloride. The primary emulsion was then added to 50 ml of distilled water containing PVA (10% w/v). This resulted in the formation of a w/o/w emulsion which was again homogenized at high speed for 4 minutes. The resulting emulsion was stirred at 1000 rpm for 12 hours at room temperature and the methylene chloride was allowed to evaporate. The microparticles were filtered, washed twice in distilled water and lyophilized.

EXAMPLE 7

Preparation of PLG-Adsorbed HSVgD2 Microspheres

Blank microparticles were prepared by a solvent evaporation technique. Briefly, the microparticles with a 0% w/w protein loading level (Blank or Placebo) were prepared by adding 2 ml of normal saline solution and emulsifying at high speed using a silverson homogenizer, with 10 ml of a 10% w/v PLG polymer solution in methylene chloride. The primary emulsion was then added to 50 ml of distilled water containing polyvinyl alcohol (10% w/v). This resulted in the formation of a w/o/w emulsion which was stirred again at high speed for 4 minutes. The resulting emulsion was stirred at 1000 rpm for 12 hours at room temperature and the methylene chloride was allowed to evaporate. The microparticles were filtered, washed twice in distilled water and lyophilized. The Blank PLG Microparticles were added to a HSVgD2 Protein solution and mixed well by shaking the suspension on a test tube shaker at room temperature for two hours. The suspension was then frozen at −80 C. The frozen suspension was lyophilized for use as an associated HSVgD2 formulation.

EXAMPLE 8

Immunogenicity of HSVgD2-Entrapped and Adsorbed Microspheres

The HSVgD2-entrapped and adsorbed microspheres, produced as described above, were intramuscularly administered to mice and the mice were boosted after 28 days. A total dose of 10 µg of the microparticles was administered. Serum was collected at 4 and 8 weeks and IgG and neutralization titers evaluated. The results are shown in Table 3. As can be seen, HSVgD2 adsorbed with microparticles gave higher neutralization titers than the HSVgD2-entrapped microparticles.

TABLE 3

| Formulation | 4 weeks post 2 | | | 8 weeks post 2 | | |
|---|---|---|---|---|---|---|
| | IgG titers | Neutralization Titers | Ratio Neut./IgG | IgG Titers | Neutralization Titers | Ratio Neut./IgG |
| HSVgD2 1 vm entrapped | $5.4 \times 10^{-5}$ | 58 | $1.04 \times 10^{-4}$ | $2.26 \times 10^5$ | 68 | $3.01 \times 10^{-4}$ |
| HSVgD2 400 nm adsorbed | $8.54 \times 10^5$ | 192 | $2.26 \times 10^{-4}$ | $2.23 \times 10^5$ | 136 | $6.10 \times 10^{-4}$ |

EXAMPLE 9

Preparation of Gag-Adsorbed and Entrapped Microspheres

Solutions used to make Gag-adsorbed 0.4 µm microparticle formulations were as follows:
(1) 4% RG 503 PLG (Boehringer Ingelheim) in dimethyl chloride.
(2) 10% PVA (ICN) in water.
(3) PBS In particular, the internal emulsion was made by adding 1.25 ml of PBS to 12.5 ml of polymer solution and homogenizing for 2.5 minutes at 23 k, using a hand-held IKA homogenizer with a small probe. The second emulsion was made by adding the internal emulsion to 50 ml of the PVA solution and homogenizing for 3 minutes using a benchtop homogenizer with a 20 mm probe at 10 K rpm. The emulsion was left stirring overnight for solvent evaporation. The formed microspheres were then filtered through a 38 µmesh, sized in the Malvern Master sizer, then washed with water by centrifugation 3 times, and lyophilized.

P24 gag was adsorbed to the microspheres as follows.

A. 5% Adsorbed Microspheres 200 mg of the lyophilized placebo microspheres were incubated with rocking overnight at room temperature, with 80 ml 0.25 mg/ml P24 gag protein in PBS. The next day, the microspheres were centrifuged and the supernatant assayed by BCA for gag concentration to determine the amount adsorbed. The microspheres were washed once with PBS and lyophilized. The lyophilized microspheres were incubated with another 40 ml 0.25 mg/ml P24 gag in PBS with rocking at room temperature overnight. Microspheres were centrifuged the next day and the supernatant was assayed for protein by BCA. The microspheres are washed once with PBS and lyophilized. The lyophilized microspheres were analyzed for total protein adsorbed by base hydrolysis.

B. 1% Adsorbed Microspheres 100 mg 0.4 µm placebo microspheres were incubated by rocking at room temperature overnight with 10 ml 0.2 mg/ml P24 gag in PBS. The next day the microspheres were centrifuged and the supernatant assayed for protein by BCA. The microspheres were washed once with PBS, lyophilized, then assayed for adsorbed protein by base hydrolysis.

EXAMPLE 10

Immunogenicity of Gag-Adsorbed Microspheres

The gag-adsorbed microspheres, produced as described in Example 9, as well as gag-encapsulated microspheres and blank microspheres as controls, were administered to mice, as described above, and CTL activity assayed two weeks following the final immunization. As shown in Tables 4 and 5, microparticles with surface presented gag (1%) induced CTL activity, while the same amount of gag-encapsulated in biodegradable particles did not. 5% surface-adsorbed gag was also better than incorporated protein for induction of CTL activity.

TABLE 4

| | | Percent specific Lysis of targets | | |
|---|---|---|---|---|
| | | Deb-assay 1 | | |
| Effector | E:T Ratio | SV/O | SV/p7g | MC/p7g |
| PLG Surface 1% | 60:1 | 3 | 23 | 1 |
| | 12:1 | 2 | 10 | 2 |
| | 2.4:1 | 1 | 3 | 1 |
| PLG encapsulted 1% | 60:1 | 0 | 1 | −1 |
| | 12:1 | 0 | 1 | 1 |
| | 2.4:1 | 0 | 1 | −1 |
| gag alone | 60:1 | 0 | 6 | 1 |
| | 12:1 | 1 | 5 | 1 |
| | 2.4:1 | 1 | 2 | 2 |
| Vaccinia gag | 60:1 | 2 | 27 | 0 |
| | 12:1 | 1 | 10 | 2 |
| | 2.4:1 | 1 | 4 | 2 |

TABLE 5

| Effector | E:T Ratio | Percent specific Lysis of targets Deb-assay 1 SV/O | SV/p7g | MC/p7g |
|---|---|---|---|---|
| PLG | 60:1 | 3 | 32 | 2 |
| Surface 5% | 12:1 | 2 | 13 | 0 |
|  | 2.4:1 | 1 | 5 | 1 |
| PLG | 60:1 | 13 | 18 | 12 |
| encapsulted 5% | 12:1 | 5 | 8 | 4 |
|  | 2.4:1 | 1 | 2 | 0 |
| gag alone | 60:1 | 5 | 9 | 4 |
|  | 12:1 | 2 | 4 | 3 |
|  | 2.4:1 | 2 | 1 | 3 |
| Vaccinia gag | 60:1 | 9 | 32 | 11 |
|  | 12:1 | 1 | 14 | 4 |
|  | 2.4:1 | 0 | 6 | 1 |

Thus, the use of antigen-adsorbed microparticles to stimulate cell-mediated immunological responses, as well as methods of making the microparticles, are disclosed. Although preferred embodiments of the subject invention have been described in some detail, it is understood that obvious variations can be made without departing from the spirit and the scope of the invention as defined by the appended claims.

We claim:

1. A method of producing a microparticle with adsorbed antigen comprising:
   (a) forming a microparticle that comprises a poly(α-hydroxy acid) by a method comprising (i) forming an emulsion comprising said poly(α-hydroxy acid), water and an organic solvent and (ii) evaporating said solvent; and
   (b) adsorbing an antigen derived from a viral pathogen to the surface of said microparticle.

2. The method of claim 1, wherein the microparticle comprises a poly(α-hydroxy acid) selected from the group consisting of poly(L-lactide), poly(D, L-lactide) and poly(D,L-lactide-co-glycolide).

3. The method of claim 2, wherein the microparticle comprises poly(D,L-lactide-co-glycolide).

4. The method of claim 1, wherein the antigen comprises HIV gp 120.

5. The method of claim 1, wherein the antigen comprises HIV p24gag.

6. The method of claim 1, wherein the antigen comprises Influenza A hemagglutinin antigen.

7. The method of claim 1 wherein said emulsion is a water-in-oil-in-water emulsion.

8. The method of claim 1, wherein said antigen comprises a hepatitis B viral antigen.

9. The method of claim 1, wherein said antigen comprises a hepatitis C viral antigen.

10. The method of claim 1, wherein said antigen comprises an influenza A viral antigen.

11. The method of claim 1, wherein said antigen comprises an HIV antigen.

12. The method of claim 1, wherein the microparticle has a diameter between 500 nanometers and 10 microns.

13. The method of any of claims 1 and 7, wherein the poly(α-hydroxy acid) is a poly(lactide-co-glycolide).

14. The method of claim 7, wherein the microparticle comprises a poly(α-hydroxy acid) selected from the group consisting of poly(L-lactide), poly(D,L-lactide) and poly(D,L-lactide-co-glycolide).

15. The method of claim 7, wherein the poly(α-hydroxy acid) is poly(D,L-lactide-co-glycolide).

16. The method of claim 7, wherein the antigen comprises HIV gp 120.

17. The method of claim 7, wherein the antigen comprises HIV p24gag.

18. The method of claim 7, wherein the antigen comprises Influenza A hemagglutinin antigen.

19. The method of claim 7, wherein said antigen comprises a hepatitis B viral antigen.

20. The method of claim 7, wherein said antigen comprises a hepatitis C viral antigen.

21. The method of claim 7, wherein said antigen comprises an influenza A viral antigen.

22. The method of claim 7, wherein said antigen comprises an HIV antigen.

23. The method of claim 7, wherein the microparticle has a diameter between 500 nanometers and 10 microns.

24. The method of any of claims 4-6,8,9,10,11, and 12, wherein the poly(α-hydroxy acid) is a poly(lactide-co-glycolide).

25. The method of claim 7, wherein said emulsion comprises an emulsion stabilizer.

26. The method of claim 25, wherein said emulsion stabilizer is polyvinyl alcohol.

* * * * *